Figure 1:
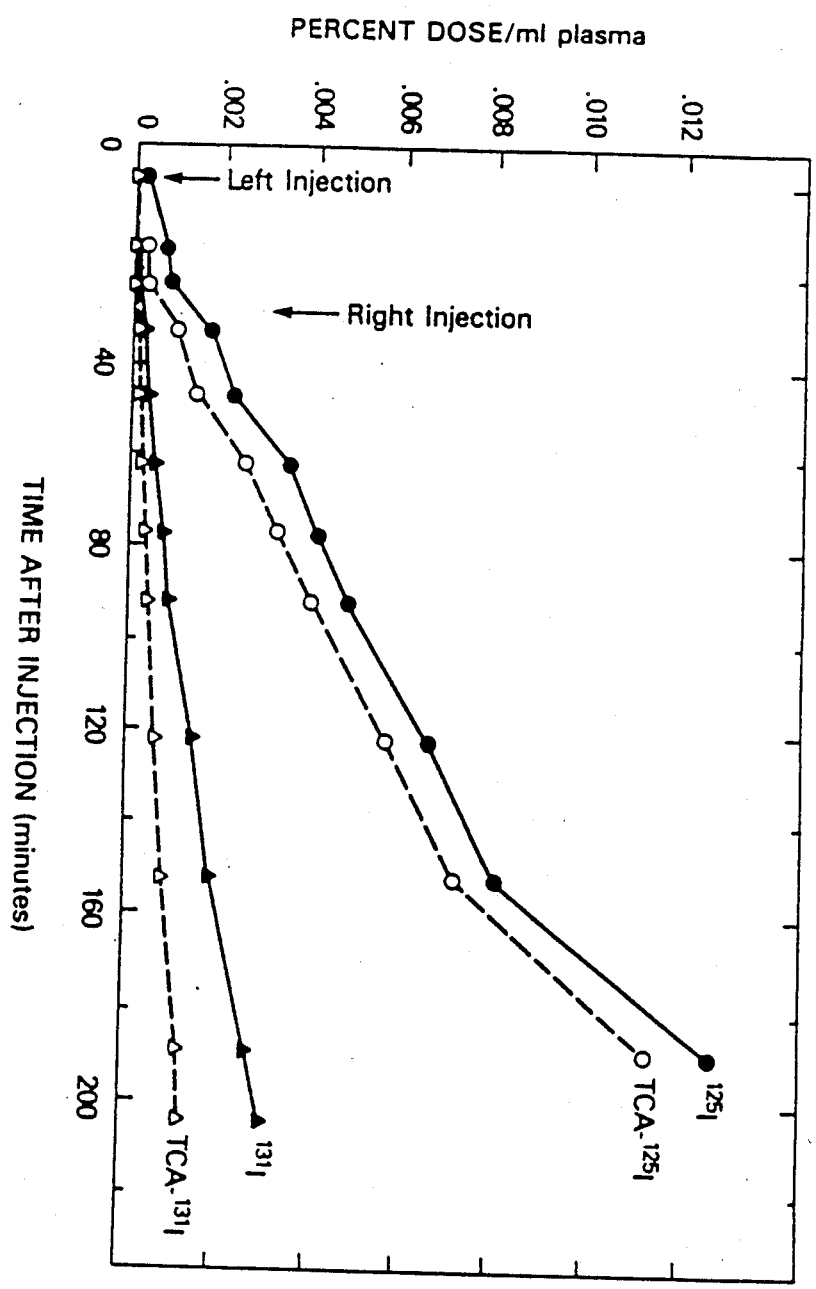

United States Patent [19]

Mulshine et al.

[11] Patent Number: 4,911,690

[45] Date of Patent: Mar. 27, 1990

[54] TREATMENT OR DIAGNOSIS BY ENDOSCOPIC ADMINISTRATION INTO THE LYMPHATICS

[75] Inventors: James L. Mulshine, Bethesda; John Weinstein, Chevy Chase, both of Md.

[73] Assignee: The United States of America as represented by the Secretary of the Department of Health and Human Services, Washington, D.C.

[21] Appl. No.: 133,978

[22] Filed: Dec. 17, 1988

Related U.S. Application Data

[63] Continuation-in-part of Ser. No. 717,615, Mar. 29, 1985, abandoned.

[51] Int. Cl.⁴ .................... A61M 31/00; A61K 49/00
[52] U.S. Cl. .................................. 604/53; 424/85.5; 424/85.8; 424/85.91; 424/1.1; 424/9; 514/2; 604/51; 604/52; 604/54
[58] Field of Search ...................... 424/85, 85.5, 85.8, 424/85.91, 9, 43, 1.1; 514/2; 604/51-53, 54

[56] References Cited

U.S. PATENT DOCUMENTS 3,927,660  12/1975  Tegtmeyer ............................ 604/51
4,714,460  12/1987  Calderon .............................. 604/53

OTHER PUBLICATIONS

Weinstein et al., Science, vol. 222 (1983), pp. 423-426.
Weinstein et al., Science, vol. 218 (1982), pp. 1334-1337.
Steller et al., Cancer Research, vol. 46 (1986), pp. 1830-1834.
Cancer Research, 47: 3572-3576 (1987).

*Primary Examiner*—Sam Rosen
*Attorney, Agent, or Firm*—Browdy and Neimark

[57] ABSTRACT

The invention provides a method of delivering therapeutic or diagnostic reagents to the lymphatic system. In the preferred method the delivery is accomplished by use of a fiberoptic endoscope equipped with an aspiration cytology needle. The method provides an especially useful means of delivering labeled monoclonal antibodies.

23 Claims, 2 Drawing Sheets

TREATMENT OR DIAGNOSIS BY ENDOSCOPIC ADMINISTRATION INTO THE LYMPHATICS

FIELD OF THE INVENTION

This application is a continuation-in-part of U.S. patent application No. 06/717,615, filed Mar. 29, 1985, now abandoned.

The present invention is directed to a method for administering diagnostic and therapeutic reagents to the lungs.

The administration of diagnostic and therapeutic reagents to the body via the lymphatic system of the lung wherein more than deminimus passage of the reagent into the blood stream occurs only after filtration through the local lymphatic nodes presents many advantages:

(1) Biologically active reagents that might bind to serum proteins or be inactivated in the body (the circulatory system, liver, or kidneys, for example) may be given in lower dosage if administered to the pulmonary lymphatic system, since greater effect can be achieved from a given dosage.

(2) Generalized, systemic toxic reactions to reagents are avoided if the reagents can be delivered directly to the target site while allowing minimal levels of reagent in the circulating blood.

(3) Many radiographic reagents which have a short half-life can be targeted to local tissue for rapid uptake and maximum effect.

(4) Administration of reagents to the lung, the fiberoptic bronchoscope equiped with an aspiration cytology needle is a highly effective means of delivery. The procedure is particularly suited for use in administration of monoclonal antibodies into the lung for purposes of detection of cells antigenic to the antibodies or for delivery of antibodies conjugated to cytotoxic reagents as therapeutic agents. The inventive methods provides an alternative to surgery as a means of making a differential diagnosis of cancer.

BACKGROUND OF THE INVENTION

The role of the lymphatic system in spread of malignancies wherein the malignant cells first invade the regional lymph nodes and then spread through the circulatory system to remote organs is well known. If the extent of metastasis of malignant cells to the lymph nodes can be accurately evaluated by the physician, he can determine more readily how best to treat the patient. The development of monoclonal antibodies possessing highly preferential binding properties has greatly improved accuracy in diagnosis of malignacies. Several U.S. patents teach methods of making such antibodies. For example, No. 4,486,538 to Bogoch and No. 4,448,890 to Smetana, et al., both of which are incorporated herein by reference, teach methods of making antibodies to detect cancer cells. However, they teach use of their products in in vitro assays. Cuttitta, et al., of this laboratory, in the text, *Monoclonal Antibodies and Cancer* edited by George White teach methods of preparing monoclonal antibodies having tumor-selective properties.

Weinstein, et al., in *Science*, Vol. 222, pages 423 to 426 teaches value of injection of antibodies into the lymph nodes to provide improved imaging. However, no endoscopic means of delivering the antibodies is taught or suggested therein.

DESCRIPTION OF THE INVENTION

The present invention is a method for administration of therapeutic and diagnostic reagents whereby the reagent is administered trans-endoscopically to the lymphatic system. This method is more effective than intravenous injection as a means of delivering reagents to the lymph nodes. The delivery of reagents to the lymph nodes by injection into the nodes has now been shown to be of greater value than subcutaneous injection as a means of delivering reagents to the lymphatic tissue. The particularly preferred method of injection is is performed through an endoscope equiped with an aspiration cytology needle. The method has been most successfully used as a means of delivering monoclonal antibodies. These antibodies may be bound to many moieties such as radiographic labels, toxins or drugs. The method may, for examples, be used to administer reagents to the peritoneum, gastrointestinal tract, pulmonary tract, or urinary tract using endoscopic equipment. The method has been particularly useful as a means of delivering reagents to the pulmonary tract using a fiberoptic bronchoscope. Reagent may be injected into the bronchi, into tissue near the bronchi, or may be delivered by aerosol onto bronchi.

The administration of selective monoclonal antibodies which react specifically with malignant cell antigens has made possible the rapid, safe imaging of lung tumors. Previously, such imaging was hampered by inactivation of antibodies for reasons previously mentioned. Furthermore, circulating antibodies widely dispersed throughout the body by means such as IV injection, produce background activity. When labeled antibodies were administered through a bronchoscope into the bronchi or interstitium of the lung, the presence of reactive antigen in tissues could be assessed in a relatively short time. (See example 1.)

It was demonstrated that antibodies injected into the lymphatics, whether through an endoscope or simply by injection through epidermal tissue, react selectively with the reactive antigen at the regional lymph nodes where binding sites are saturated. Antibodies not bound at the immediate lymph node sites pass to the more distant nodes and eventually enter the systemic circulation.

The preferential saturation at the regional lymphnodes which provides maximum regional effect prevents extensive interaction of antibodies with other antigens in the circulating blood or non-lymphatic cells. The specificity of binding when antibodies are administered in accord with the invention has made possible clinical use of antibodies which were previously ineffective. This advantage is seen as especially important in the treatment of lung cancer, since monoclonal antibodies to malignancies of the lung are characterized by cross-reactivity (lack of specificity) when administered via other routes.

When the therapeutic reagent is a cytotoxin, whether or not that toxin is bound to an antibody, it is important that healthy cells be exposed to a minimal amount of toxin. The instant invention provides a method of exposing diseased cells to the toxin while exposing normal cells to minimal risk. As examples of cytotoxic compositions suitable for administration by this method, see U.S. Pat. No. 4,545,985 to Pastan, et al. or U.S. Pat. No. 4,340,535 to Voisen, et al., both of which are incorporated herein by reference.

The range of reagents which can be administered is extensive and includes interleukin 2, interferon, antimicrobials, tumor necrosis factor, growth factors, and growth factor antagonists. One of ordinary skill in the art would readily understand the above examples are given for illustration. No limitation should be presumed therefrom.

DRAWINGS

FIG. 1 shows plasma levels of iodine-131 and iodine-125 after intrabronchial injection of $^{131}$I-labeled specific antibody (ISCR3) and corresponding values for $^{125}$I-labeled irrelevant monoclonal antibody 36.7.5) in a dog that received 600 μCi of total radioactivity. ● total counts; O, plasma protein-associated counts; arrows, times of injection.

Figure 2:
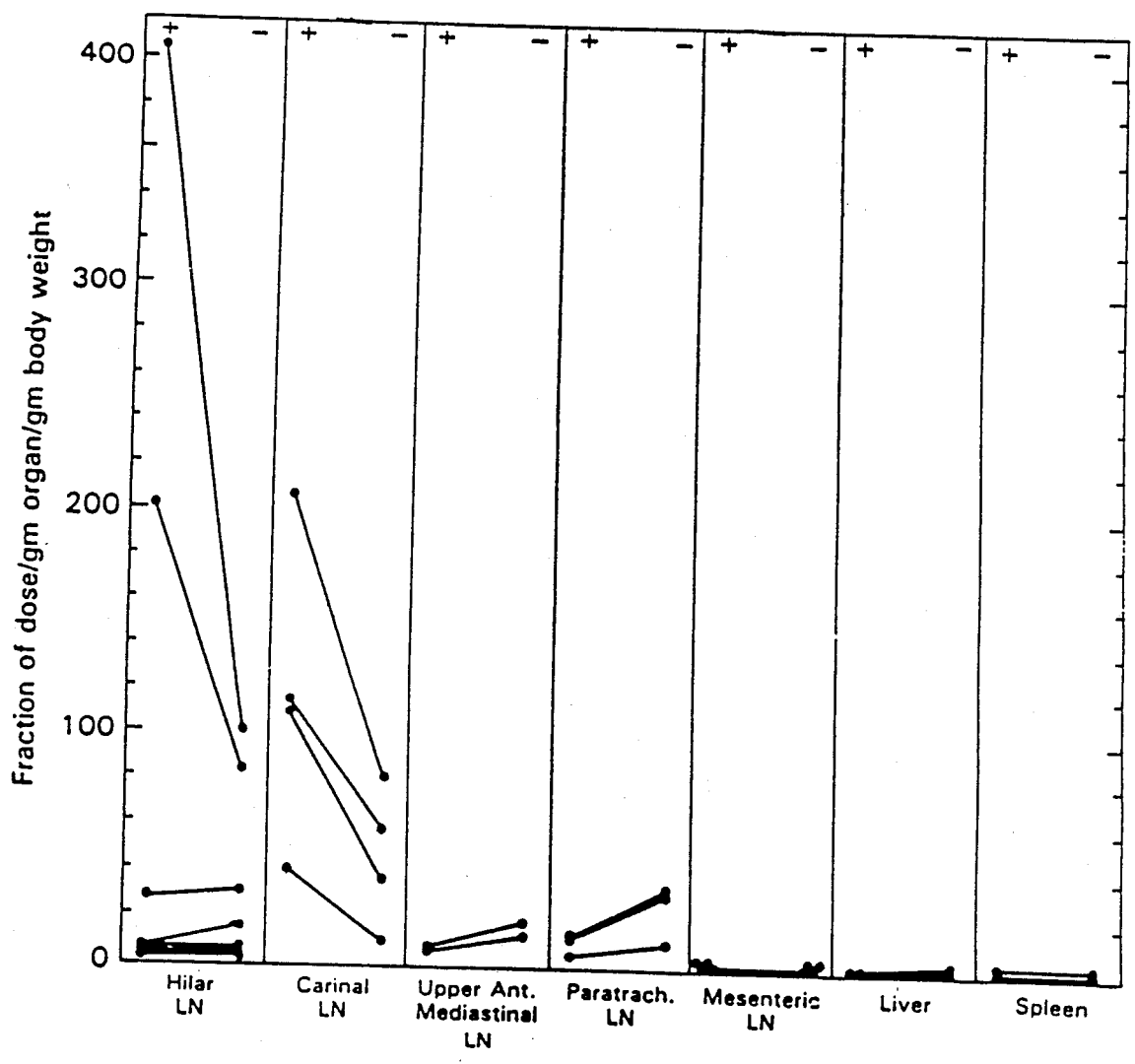

FIG. 2 shows analysis of radioactivity from pulmonary lymph nodes, liver, and spleen after injection via bronchoscope of specific iodine-131 (+) and nonspecific iodine-125 (−) expressed as fraction of dose per gram of organ normalized by the body weight. For each individual organ a line connects the data points for (+) and nonspecific (−) activity to allow evaluation of the selectivity. Regional lymph nodes that received large amounts of antibody (and blue dye) showed favorable selectivity ratios.

EXAMPLES

Example 1

Radiolabeled monoclonal antibodies were injected via a flexible bronchoscope through the mucosa of subsegmental bronchi in normal dogs. The antibodies were $^{131}$I-labeled murine IgG$_2$ anti-mouse I-E$^K$, also reactive with dog Ia-bearing cells. An $^{125}$I-labeled non-specific antibody was used as a control. Anesthetized dogs were intubated, bronchoscoped, and co-injected with the two antibodies (600 micro Ci/100 micro gram total). The animals were serially imaged and autopsied 12-36 hours after injection. Hilar and carinal lymph nodes contained over 1% of the injected doses, an amount greater than the activity in the mediastinal lymph nodes, and much greater than the activity in distal sites (liver, spleen, bone marrow, and lung paranchyma other than at the injection site). The ratio of $^{131}$I counts between hilar/carinal lymph nodes and non-regional (abdominal) lymph nodes ranged from 1:15 to 1:100.

Example 2

Using local anesthesia a fiberoptic bronchoscope was passed through the nose of a supine patient. The tracheobronchial tree was visualized. The patient had a large tumor mass in the right upper lobe and that area was localized. In an area of normal bronchus just distal to the tumor the radiolabeled antibody was injected. The radiolabeled material was mixed with a low concentration of Evans Blue Dye (so the material could be directly visualized). The patient tolerated the injection with no apparent acute effects. The injectate raised a small vesicle which would result in slight extravasation of the injectate. The patient was then serially scanned with a gamma camara over multiple tune points for the next week. The results of the imaging were stored on a computer to permit full analysis.

The antibody used for this procedure was the 2A11, an IgG, antigastrum-releasing peptide which was conjugated using a modified DPTA chelate to indium-111. Table 1 shows the whole body clearance (percent of dose in the body) at various durations after administration.

TABLE 1

| post-injection hours | IV injection % in body | Administration into Bronchial lymph nodes % in body |
|---|---|---|
| 0 | 100 | 100 |
| 24 | 72.586 | 101 |
| 48 | 55.5 | 95.673 |
| 168 | — | 57.593 |

As can be seen from the above data, the injectate administered to the bronchial lymph nodes by the method of Example 2 remained in the body for the much longer time. Such data indicates the more effective binding of the antibody to the tissue when the method of the invention is used.

What we claim is:

1. A process for delivering therapeutric or diagnostic reagents directly to the lymphatics comprising the steps of:
   (1) inserting an endoscope into a body passage or cavity, and
   (2) administering the reagent through the endoscope into tissues for uptake by the lymphatic vessels.

2. A process according to claim 1 for delivering a composition containing therapeutic and/or diagnostic reagents to tissues for uptake by lymphatic vessles comprising the steps of:
   (1) inserting an endoscope into a body passage or cavity in the location of tissues near the terminal lymphatic vessels, and
   (2) administering the composition by injection into tissues in the area of the terminus of the lymphatic vessels.

3. A process according to claim 2 wherein the endoscope is a fiberoptic bronchoscope.

4. A process according to claim 3 wherein the injection is accomplished by use of an aspiration cytology needle.

5. A process according to claim 2 wherein the injectate contains a monoclonal antibody.

6. A process according to claim 5 wherein the antibody is a radiolabeled antibody.

7. A process according to claim 4 wherein the injectate contains a monoclonal antibody.

8. A process according to claim 2 wherein the composition comprises an antigastrum-releasing peptide antibody.

9. A process according to claim 1 wherein the reagent is delivered as an aerosol.

10. A process according to claim 1 wherein the reagent is an antibody conjugate.

11. A process according to claim 2 wherein the composition contains an antibody conjugate.

12. A process according to claim 10 wherein the antibody is conjugated to a cytotoxin.

13. A process according to claim 11 wherein the antibody is conjugated to a cytotoxin.

14. A process according to claim 10 wherein the antibody is conjugated to a differentiation agent.

15. A process according to claim 11 wherein the antibody is conjugated to a differentiation agent.

16. A process according to claim 10 wherein the antibody is conjugated to an immunotoxin.

17. A process according to claim 11 wherein the antibody is conjugated to an immunotoxin.

18. A process according to claim 10 wherein the antibody is conjugated to a radionucleotide.

19. A process according to claim 11 wherein the antibody is conjugated to a radionucleotide.

20. A process according to claim 1 wherein the reagent contains an immunoglobulin fragment.

21. A process according to claim 2 wherein the composition contains an immunoglobulin fragment.

22. A process according to claim 1 wherein the reagent contains a genetically engineered derivative of an immunoglobulin molecule.

23. A process according to claim 2 wherein the composition contains a genetically engineered derivative of an immunoglobulin molecule.

* * * * *